US006887564B2

(12) United States Patent
Gagliardini et al.

(10) Patent No.: US 6,887,564 B2
(45) Date of Patent: May 3, 2005

(54) ARTICLES COMPRISING CHITOSAN MATERIAL AND AN ANIONIC ABSORBENT GELLING MATERIAL

(75) Inventors: Alessandro Gagliardini, Jesi (IT); Giovanni Carlucci, Chieti (IT); Achille Di Cintio, Pescara (IT); Antonella Pesce, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 268 days.

(21) Appl. No.: 10/251,071

(22) Filed: Sep. 20, 2002

(65) Prior Publication Data

US 2003/0049480 A1 Mar. 13, 2003

Related U.S. Application Data

(63) Continuation of application No. PCT/US01/13157, filed on Apr. 24, 2001.

(30) Foreign Application Priority Data

Apr. 25, 2000 (EP) .............................................. 00108063

(51) Int. Cl.[7] .............................................. B23B 5/22
(52) U.S. Cl. ................................ 428/317.8; 428/537.5; 428/304.4; 428/311.11; 428/402; 442/153; 442/167; 442/168; 442/171; 604/366; 604/367

(58) Field of Search ....................... 428/317.9; 442/153, 442/167, 168, 171; 604/366, 367

(56) References Cited

U.S. PATENT DOCUMENTS

| 4,043,952 A | * | 8/1977 | Ganslaw et al. ............. 524/399 |
| 4,654,039 A | * | 3/1987 | Brandt et al. ................ 604/368 |
| 5,496,933 A | * | 3/1996 | Kelkenberg ................... 536/20 |
| 5,853,867 A | * | 12/1998 | Harada et al. ............ 428/317.9 |
| 5,932,495 A | | 8/1999 | Boney |

FOREIGN PATENT DOCUMENTS

| EP | 0 811 392 A1 | 12/1997 |
| GB | 2 292 526 A | 2/1996 |
| WO | WO 91/12029 A1 | 8/1991 |
| WO | WO 99/32697 A2 | 7/1999 |
| WO | WO 99/55393 A1 | 11/1999 |

* cited by examiner

Primary Examiner—Leszek Kiliman
(74) Attorney, Agent, or Firm—Kevin C. Johnson; Bridget D. Murray

(57) ABSTRACT

The present invention relates to articles, preferably disposable absorbent articles like sanitary napkins and pantiliners, which comprise a chitosan material and an anionic absorbent gelling material. Such disposable absorbent articles deliver improved odor control performance and improved fluid handling properties/absorption performance, especially in case of electrolytes-containing fluids like menses.

21 Claims, 1 Drawing Sheet

ARTICLES COMPRISING CHITOSAN MATERIAL AND AN ANIONIC ABSORBENT GELLING MATERIAL

CROSS REFERENCE TO RELATED REFERENCES

This is a continuation of International Application PCT/US01/13157 with an International filing date of Apr. 24, 2001.

FIELD OF THE INVENTION

This invention relates to articles, such as disposable absorbent articles, comprising chitosan material together with an anionic absorbent gelling material.

BACKGROUND OF THE INVENTION

A wide variety of materials have been described for use as absorbent gelling materials in disposable absorbent articles. Such materials include natural-based materials such as agar, pectin, gums, carboxyalkyl starch and carboxyalkyl cellulose as well as synthetic materials such as polyacrylates, polyacrylamides and hydrolyzed polyacrylnitrile. While the natural-based absorbent gelling materials are known for use in such hygienic absorbent articles, they have not gained wide usage in such articles. The natural-based absorbent gelling materials have not gained wide usage in absorbent articles, at least in part, because their absorbent properties are generally inferior compared to synthetic absorbent gelling materials, such as the polyacrylates. Most of the commercially available disposable absorbent articles for body care like sanitary napkins and diapers comprise synthetic absorbent gelling materials, typically polyacrylates, to deliver body fluid absorption and retention characteristics. However although such synthetic absorbent gelling materials exhibit outstanding absorption capacity towards de-ionized water, their absorption capacity towards electrolytes/salts-containing solutions like menses is lower. It is generally believed that this effect results from the electrolyte content of body fluids and this effect is often referred to as 'salt poisoning'.

The water absorption and water retention characteristics of synthetic absorbent gelling materials are due to the presence in the polymer structure of ionisable functional groups. These groups are usually carboxyl groups, a high proportion of which are in the salt form when the polymer is dry but which undergo dissociation and salvation upon contact with water. In the dissociated state, the polymer chain will have a series of functional groups attached to it which groups have the same electric charge (e.g., —COO⁻ -OOC—) and thus repel one another. This leads to expansion of the polymer structure, which, in turn permits further absorption of water molecules although this expansion is subject to the constraints provided by the cross-links in the polymer structure, which must be sufficient to prevent dissolution of the polymer. It is assumed that the presence of a significant concentration of electrolytes in the water like in menses or urine or milk discharge interferes with the dissociation of the functional groups and leads to the 'salt poisoning effect'. This salt poisoning effect is detrimental to the absorption capacity of the polymer.

It is thus a need to provide absorbent articles with improved absorption performance in the presence of electrolytes, for example in the case of menses or lactational fluid.

Whilst the primary focus of absorbent articles, in particular feminine hygienic absorbent articles like sanitary napkins, breast pads and pantiliners, remains the ability of these articles to absorb and retain fluids, another important area of development in this field is the control of odorous compounds contained within the absorbent articles during their use.

The presence and detection of malodorous compounds from absorbent articles during their use, particularly those associated with menstruation may cause the wearer of these articles embarrassment. Thus, the prevention of the detection of malodor from such articles is highly desirable too.

In use, the absorbent articles are known to acquire a variety of compounds, for example volatile fatty acids (e.g. isovaleric acid), ammonia, amines (e.g. triethylamine), sulphur containing compounds (e.g. mercaptans, sulphides), alcohols, ketones and aldehydes (e.g., furaldehyde) which release unpleasant odors. These compounds may be present in the bodily fluid or may be developed by chemical reactions and/or any fluid degradation mechanisms once the bodily fluid is absorbed into the absorbent article like for example a feminine hygienic absorbent article. In addition bodily fluids usually contain microorganisms and/or enzymes that can also generate malodorous by products as a result of degradation mechanisms like putrefactive degradation, acid degradation, proteins degradation, fat degradation and the like.

Various odor control materials have been disclosed in the art to combat some of the unpleasant odors referred to above. Indeed solutions have been provided that use different technical approaches like masking, i.e., covering the odor with a perfume, or absorbing the odor already present in the bodily fluids and those generated after degradation, or preventing the formation of the odor.

Most of the focus in the prior art is found on the odor absorption technology. Examples of these types of compounds include activated carbons, clays, zeolites, silicates, cyclodextrine, ion exchange resins and various mixture thereof as for example described in EP-A-348 978, EP-A-510 619, WO 91/12029, WO 91/11977, WO89/02698, and/or WO 91/12030. All of these types of odor control agents are believed to control odor by mechanisms whereby the malodorous compounds and their precursors are physically absorbed by the agents and thereby hinder the exit of the odor from articles like absorbent articles. However, such mechanisms are not completely effective as the formation of the odor itself is not prevented and thus odor detection is not completely avoided.

Thus although these materials provide some control of odors associated with bodily fluids, there still exists a need of further improvement in terms of odor control of malodors which are generated by the human body, or from bodily fluids such as perspiration, urine, faeces, menstrual fluids, vaginal fluids, lactational fluid and the like.

More particularly, it is an object of the present invention to provide articles, especially disposable absorbent articles, which deliver a broader spectrum of odor control while delivering a high protection level. Actually it is an object of the present invention to provide articles, especially disposable absorbent articles, with improved odor control properties and improved fluid absorption performance especially in the presence of electrolytes-containing solutions for example in the case of menses or urine or lactational fluid.

It has now surprisingly been found that the combination of chitosan material together with an anionic absorbent gelling material in an article, like an absorbent article typically coming into contact with bodily fluid, delivers both improved odor control performance over a broad range of malodors compounds and improved absorption performance. Indeed this combination has been found to be particularly effective in the case of electrolytes-containing solutions like menses or urine or lactational fluid.

More particularly, it has surprisingly been found that the addition of an anionic absorbent gelling material on top of chitosan material results in a synergistic effect in terms of odor control. Indeed, this combination gives more odor reduction than the odor reduction associated with the use of one of these two classes of ingredients alone at the same total level (either chitosan material alone or the absorbent gelling material alone) in an absorbent article coming into contact with bodily fluids.

Actually the combination of chitosan material with an anionic absorbent gelling agent allows to combine odor control mechanisms by which the overall malodor detection is synergistically reduced or even prevented.

Without to be bound by any theory it is believed that chitosan material provides odor control of malodors components associated with bodily fluid by multiple mechanisms.

Firstly, the odor absorption and retention characteristics of chitosan materials are due to the presence in the polymer structure of ionisable cationic functional groups. These groups are usually ammonium groups, a high proportion of which are in the salt form when the polymer is dry but which undergo dissociation and salvation upon contact with bodily fluid. In the dissociated state, the polymer chain will have a series of functional groups attached to it which groups have the same electric charge (e.g., $-NH_3^+$ $^+H_3N-$) and thus repel one another. This leads to expansion of the polymer structure, which, in turn permits further absorption of negatively charged odorous molecules and thus the control thereof.

Secondly, the positively charged cationic groups of the chitosan materials will interact with negatively charged anionic groups-bearing molecules present in bodily fluids, like the carboxylic groups of proteins or hydroxylic acid bearing entities like short chain acid (e.g., butyric acid). This will result in the formation of tri-dimensional net between chitosan materials and such molecules with anionic groups (gelification of the bodily fluids). This gelification will entrap most odorous molecules (like lipids, acids) thereby controlling malodor.

Thirdly and more importantly the chitosan materials are believed to act as antimicrobial agents. Indeed the chitosan materials with their positively charged cationic groups will interfere with negatively charged surface of microorganism walls, thereby inhibiting the growth of such microorganisms or even killing such microorganisms. These chitosan materials will also interfere with negatively charged surface of enzymes, thereby inactivating the enzymatic activity, which, like the microbial activity, are otherwise responsible for the formation of malodorous components. The chitosan materials further act by their indirect antimicrobial activity by linking some of the microorganism nutriments like lipids and/or minerals.

In a preferred embodiment of the present invention the chitosan materials used are chitosan salts. Without to be bound by theory it is speculated that chitosan salts, due to a higher percentage of positively charged cationic groups, delivers all above mentioned benefits immediately upon contact with bodily fluids.

Advantageously the presence of the anionic absorbent gelling material boosts the odor controlling properties of chitosan materials. More generally, the anionic absorbent gelling materials increase the cationic properties of chitosan materials which result in enhanced antimicrobial activity, enhanced absorption activity and enhanced gelification properties. Without to be bound by any theory it is believed that the carboxylic groups of the absorbent gelling materials protonate the amino groups of the chitosan materials, enhancing thereby the numbers of positively charged ammonium groups ($-NH_3^+$) of the chitosan materials and thus the cationic character of the chitosan materials.

The use of chitosan materials together with anionic absorbent gelling materials, preferably synthetic absorbent gelling materials, in absorbent articles also provides improved body fluid absorbing performance not only towards water but especially towards electrolyte-containing fluids. More generally, this combination, when used in absorbent articles, provides enhanced fluid handling properties, i.e., not only improved absorption performance towards water and especially towards electrolytes-containing fluids, this even under pressure conditions, but also reduced wetting through (i.e., reduced fluid leakage) and reduced rewetting of the topsheet.

In a preferred embodiment of the present invention the article comprises chitosan salts, preferably water-soluble chitosan salts, together with anionic absorbent gelling material, preferably having a degree of neutralization of 50% to 90%, to provide both optimum odor control properties and fluid handling properties. Advantageously, these properties are delivered immediately upon exposure of the article to bodily fluids and last for a prolonged wearing time of the article by the user. Without the intention to be bound by any theory it is speculated that these benefits are due to the availability of higher percentages of positively charged cationic groups of the chitosan salt upon contact with bodily fluids (compared for example to chitosan base material) as well as to the properties of the absorbent gelling material to further increase the percentage of positively charged groups of the chitosan salt, thereby maintaining all previously mentioned benefits upon a prolonged wearing time of the article.

The present invention is preferably directed to disposable absorbent articles like pantiliners, feminine napkins, incontinent pads, diapers, tampons, interlabial pads, perspiration pads, surgical pads, breast pads, human or animal waste management devices and the like. Other articles suitable for use according to the present invention further include articles designed to be placed against or in proximity to the body such as clothing, bandages, thermal pads, acne pads, cold pads, compresses, surgical pads/dressings and the like, body cleansing articles like impregnated wipes/tissues (e.g. baby wipes, wipes for feminine intimate hygiene), articles for absorbing perspiration such as shoe insoles, shirt inserts, and the like, and articles for animals like litters and the like.

BACKGROUND ART

WO99/61079, discloses odor reduction for products such as disposable diapers and training pants, sanitary napkins and tampons by the use of triglycerides and polyglycosides to enhance the malodor absorption properties of compositions and substrates such as naturally occurring polymers like chitosan or alginates and synthetic polymers treated with surfactants.

WO99/32697 discloses that chitosan and chitin-based polymers exhibit increased antimicrobial activity when coated onto the surface of a hydrophobic material such as polypropylene.

Other references further disclose the use of chitosan materials in absorbent articles like WO96/20015, JP1182302 or JP620648.

None of these references discloses absorbent articles comprising chitosan material together with anionic absorbent gelling material, let alone the improved odor control performance associated with this combination while providing improved fluid-absorption, especially in the case of electrolytes containing fluids, like menses and urine.

BRIEF DESCRIPTION OF THE DRAWINGS

The invention is further described with reference to the accompanying drawings.

SUMMARY OF THE INVENTION

The present invention relates to an article, preferably a disposable absorbent article, comprising chitosan material together with an anionic absorbent gelling material.

The present invention also encompasses a method of controlling odor associated with bodily exudates and/or bodily fluids, wherein said bodily exudates and/or fluids are contacted with an odor control system comprising chitosan material together with an anionic absorbent gelling material. Typically the bodily fluids/exudates comes in contact with an absorbent article suitable to be placed against or in proximity to the body of the wearer, said article comprising an odor control system comprising chitosan material together with an anionic absorbent gelling material

DETAILED DESCRIPTION OF THE INVENTION

By "article" it is meant herein any three-dimensional solid material being able to comprise chitosan material and an anionic absorbent gelling material. The term "disposable" is used herein to describe articles, which are not intended to be launched or otherwise restored or reused as an article (i.e., they are intended to be discarded after a single use and, preferably to be recycled, composted or otherwise disposed of in an environmentally compatible manner). The term "absorbent article" is used herein in a very broad sense including any article able to receive and/or absorb and/or contain and/or retain fluids and/or exudates, especially bodily fluids/bodily exudates.

Preferred articles according to the present invention are disposable absorbent articles that are designed to be worn in contact with the body of a user and to receive fluids discharged from the body, such as pantiliners, sanitary napkins, catamenials, incontinence inserts/pads, diapers, tampons, interlabial pads/inserts, breast pads, human or animal waste management devices and the like. Typically such human urine or faecal management devices comprise a bag having an aperture and a flange surrounding the aperture for preferably adhesive attachment to the urogenital area and/or the perianal area of a wearer. Any faecal or urine management device known in the art is suitable for use herein. Such devices are described in for example WO 99/00084 to WO 99/00092. Other suitable articles according to the present invention also include other articles designed to be placed against or in proximity to the body such as clothing, bandages, thermal pads, acne pads, cold pads, compresses, surgical pads/dressings and the like, articles for absorbing perspiration such as shoe insoles, shirt inserts, perspiration pads and the like, body cleansing articles like impregnated wipes/tissues (e.g. baby wipes, wipes for feminine intimate hygiene), and the like, and articles for animals like litters and the like.

By "bodily fluids and/or bodily exudates" it is meant herein any fluid/exudate produced by human or animal body occurring naturally or accidentally like for instance in the case of skin cutting, including for instance perspiration, urine, menstrual fluids, faeces, vaginal secretions, lactational fluid in the case of breast pads for lactating women and the like.

Chitosan Materials

According to the present invention the articles comprise as an essential component a chitosan material or a mixture thereof.

By 'chitosan material' it is meant herein chitosans, modified chitosans, crosslinked chitosans and chitosan salts.

Chitosan is a partially or fully deacetylated form of chitin, a naturally occurring polysaccharide. Indeed, chitosan is an aminopolysaccharide usually prepared by deacetylation of chitin (poly-beta(1,4)-N-acetyl-D-glucosamine).

Chitin occurs widely in nature, for example, in the cell walls of fungi and the hard shell of insect and crustaceans. The waste from shrimp, lobster, and crab seafood industries typically contains about 10 to about 15 percent chitin and is a readily available source of supply. In the natural state, chitin generally occurs only in small flakes or short fibrous material, such as from the carapace or tendons of crustaceans. There is generally no source, as with cotton in the cellulosics, that forms useful shaped articles without solution and re-precipitation or re-naturing.

More specifically, chitin is a mucopolysaccharide, poly-N-acetyl-D-glucosamine with the following formula:

wherein x represents the degree of polymerization. Although x cannot be determined precisely, x is believed to be commonly in the range of from about 30 to about 50,000.

Chitosan is not a single, definite chemical entity but varies in composition depending on the conditions of manufacture. It may be equally defined as chitin sufficiently deacetylated to form soluble amine salts. Chitosan is the beta-(1–4) polysaccharide of D-glucosamine, and is structurally similar to cellulose, except that the C-2 hydroxyl group in cellulose is substituted with a primary amine group in chitosan. The large number of free amine groups makes chitosan a polymeric weak base. Solutions of chitosan are generally highly viscous, resembling those of natural gums.

The chitosan used herein is suitably in relatively pure form. Methods for the manufacture of pure chitosan are well known. Generally, chitin is milled into a powder and demineralized with an organic acid such as acetic acid. Proteins and lipids are then removed by treatment with a base, such as sodium hydroxide, followed by chitin deacetylation by treatment with concentrated base, such as 40 percent sodium hydroxide. The chitosan formed is washed with water until the desired pH is reached.

The properties of chitosan relate to its polyelectrolyte and polymeric carbohydrate character. Thus, it is generally insoluble in water, in alkaline solutions at pH levels above about 6.5, or in organic solvents. It generally dissolves readily in dilute solutions of organic acids such as formic, acetic, tartaric, glycolic, lactic and citric acids, and also in dilute mineral acids, except, for example, sulfuiric acid. In general, the amount of acid required to dissolve chitosan is approximately stoichiometric with the amino groups. Since the pKa for the amino groups present in chitosan is between 6.0 and 7.0, they can be protonated in very dilute acids or even close to neutral conditions, rendering a cationic nature to this biopolymer. This cationic nature is the basis of many of the benefits of chitosan. Indeed, chitosan material can be considered as a linear polyelectrolyte with a high charge density which can interact with negatively charged surfaces, like proteins (e.g., by interfering with the proteinic wall construction of microorganisms, thereby acting as an antimicrobial agent and/or by reacting with the proteins present in bodily fluid, like menses, thereby acting as a gelifying agent for such fluid) or like anionic absorbent gelling materials, thereby further enhancing the cationic properties of the chitosan materials, or like anionic salts, thereby reducing the salt poisoning effect and thus providing outstanding absorption properties even in presence of electrolyte-containing solutions like menses or lactational fluid.

Preferred chitosan materials for use herein have an average degree of deacetylation (D.A.) of more than 75%, preferably from 80% to about 100%, even more preferably from 90% to 100% and most preferably from 95% to about 100%. The degree of deacetylation refers to the percentage of the amine groups that are deacetylated. This characteristic is directly related to the hydrogen bonding existing in this biopolymer, affecting its structure, solubility and ultimately its reactivity. The degree of deacethylation can be determined by titration, dye adsorption, UV-VIS, IR, and NMR spectroscopy.

The degree of deacetylation will influence the cationic properties of chitosan. By increasing the degree of deacetylation the cationic character of chitosan material will increase and thus its antimicrobial, its absorbing ability and its gelifying ability.

Suitable chitosan materials to use herein include both water-soluble and water insoluble chitosan. As used herein, a material will be considered to be water-soluble when it substantially dissolves in excess water to form a clear and stable solution, thereby, losing its initially particulate form and becoming essentially molecularly dispersed throughout the water solution. Preferred chitosan materials for use herein are water soluble, i.e., at least 0.5 gram and preferably at least 1 gram of the chitosan materials are soluble in 100 grams of water at 25° C. and one atmosphere. By "solubility" of a given compound it is to be understood herein the amount of said compound solubilised in de-ionized water at 25° C. and one atmosphere in absence of precipitate.

As a general rule, the water-soluble chitosan materials will be free from a substantial degree of crosslinking, as crosslinking tends to render the chitosan materials water insoluble.

Water-soluble chitosan materials as defined herein are preferred as they have the benefit to be more active in terms of odor control towards most of the malodorous compounds present and soluble in bodily fluid. Indeed such water-soluble chitosan materials have the ability to absorb and/or electrostatically interfere with water-soluble malodorous components like short chain acid (e.g., butyric acid) or low molecular weight alcohol (e.g., ethanol).

Chitosan materials (i.e., chitosan and -chitosan salts, modified chitosans and cross-linked chitosans) may generally have a wide range of molecular weights. Chitosan materials with a wide range of molecular weights are suitable for use in the present invention, typically chitosan materials for use herein have a molecular weight ranging from 1 000 to 10 000 000 grams per gram moles and more preferably from 2 000 to 1 000 000. Molecular weight means weight average molecular weight. Methods for determining the weight average molecular weight of chitosan materials are known to those skilled in the art. Typical methods include for example light scattering, intrinsic viscosity and gel permeation chromatography. It is generally most convenient to express the molecular weight of a chitosan material in terms of its viscosity in a 1.0 weight percent aqueous solution at 25° C. with a Brookfield viscometer. It is common to indirectly measure the viscosity of the chitosan material by measuring the viscosity of a corresponding chitosan salt, such as by using a 1.0 weight percent acetic acid aqueous solution. Chitosan materials suitable for use in the present invention will suitably have a viscosity in a 1.0 weight percent aqueous solution at 25° C. of from about 1 mPa·s (1 centipoise) to about 80,000 mPa·s (80,000 centipoise), more suitably from about 30 mPa·s (30 centipoise) to about 10,000 mPa·s (10,000 centipoise), even more suitably from 50 mPa·s (50 centipoise) to about 1,000 mPa·s (1,000 centipoise) and most suitably from 100 mPa·s (100 centipoise) to about 500 mPa·s (500 centipoise).

Chitosan materials pH depends on the preparation of the chitosan materials. Preferred chitosan materials for use herein have an acidic pH, typically in the range of 3 to 6, more preferably from 4 to 5.5 and even more preferably from 4.5 to 5.5. Highly preferred pH is around pH 5, which corresponds to the skin pH. By pH of chitosan material it is meant herein the pH of a 1% chitosan solution (1 gram of chitosan material dissolved in 100 grams of distilled water) measured by pH-meter.

By using more acidic pH, the cationic character of chitosan materials will be increased and thus their antimicrobial properties, absorbing ability and gelifying ability. However too high acidity is detrimental to skin safety. Thus it is highly preferred herein to use chitosan materials with a pH in the range of 4.5 to 5.5, thereby delivering the best compromise between odor control and fluid handling properties on one side and skin compatibility on the other side.

Particularly suitable chitosan materials for use herein are chitosan salts, especially water-soluble chitosan salts. The antimicrobial properties, absorbing ability and gelifying abilities of the chitosan salt are available immediately after exposure to bodily fluids. A variety of acids can be used for forming chitosan salts. Suitable acids for use are soluble in water or partially soluble in water, are sufficiently acidic to form the ammonium salt of chitosan and yet not sufficiently acidic to cause hydrolysis of chitosan, and are present in amount sufficient to protonate the reactive sites of chitosan.

Preferred acids can be represented by the formula:

wherein n has a value of 1 or 2 or 3 and R represents a mono- or divalent organic radical composed of carbon, hydrogen and optionally at least one of oxygen, nitrogen and sulfur or simply R is a hydroxyl group. Preferred acids are the mono- and dicarboxylic acids composed of carbon, hydrogen, oxygen and nitrogen (also called herein after amino acids). Such acids are highly desired herein as they are biologically acceptable for use against or in proximity to the human body. Illustrative acids, in addition to those previously mentioned include, among others, citric acid, formic acid, acetic acid, N-acetylglycine, acetylsalicylic acid, fumaric acid, glycolic acid, iminodiacetic acid, itaconic acid, lactic acid, maleic acid, malic acid, nicotinic acid, 2-pyrrolidone-5-carboylic acid, salycilic acid, succinamic acid, succinic acid, ascorbic acid, aspartic acid, glutamic acid, glutaric acid, malonic acid, pyruvic acid, sulfonyldiacetic acid, benzoic acid, epoxysuccinic acid, adipic acid, thiodiacetic acid and thioglycolic acid. Any chitosan salts formed from the reaction of chitosan with any of these acids are suitable for use herein.

Examples of chitosan salts formed with an inorganic acid include, but are not limited to, chitosan hydrochloride, chitosan hydrobromide, chitosan phosphate, chitosan sulphonate, chitosan chlorosulphonate, chitosan chloroacetate and mixtures thereof. Examples of chitosan salts formed with an organic acid include, but are not limited to, chitosan formate, chitosan acetate, chitosan lactate, chitosan glycolate, chitosan malonate, chitosan epoxysuccinate, chitosan benzoate, chitosan adipate, chitosan citrate, chitosan salicylate, chitosan propionate, chitosan nitrilotriacetate, chitosan itaconate, chitosan hydroxyacetate, chitosan butyrate, chitosan isobutyrate, chitosan acrylate, and mixtures thereof. It is also suitable to form a chitosan salt using a mixture of acids including, for example, both inorganic and organic acids.

Highly preferred chitosan salts for use herein are those formed by the reaction of chitosan with an amino acid. Amino acids are molecules containing both an acidic and amino functional group. The use of amino acids is highly preferred as those chitosan amino salts have higher skin compatibility. Indeed most of the amino acids are naturally present on the skin. Chitosan salts of pyrrolidone carboxylic acid are effective moisturizing agents and are non-irritating to skin.

Amino acids for use herein include both linear and/or cyclo amino acids. Examples of amino acids for use herein include, but are not limited to, alanine, valine, leucine, isoleucine, prolinephenylalanine, triptofane, metionine, glycine, serine, cysteine, tyrosine, asparagine, glutamine, aspartic acid, glutamic acid, lysine, arginine, istydine, hydroxyproline and the like. A particularly suitable example of cyclo amino acid is pyrrolidone carboxylic acid, which is a carboxylic acid of pyrrolidin-2-one as per following formula:

Reference is made to WO98/07618, which describes in details processes for the preparation of such chitosan salts.

Other chitosan materials suitable for use herein include cross-linked chitosans and modified chitosans.

Suitable crosslinking agents for use herein are organic compounds having at least two functional groups or functionalities capable of reacting with active groups located on the chitosan materials. Examples of such active groups include, but are not limited to, carboxylic acid (—COOH), amino (—NH$_2$), or hydroxyl (—OH) groups. Examples of such suitable crosslinking agents include, but are not limited to, diamines, polyamines, diols, polyols, dicarboxylic acids, polycarboxylic acids, aminocarboxylic acids, aminopolycarboxylic acids, polyoxides and the like. One way to introduce a crosslinking agent with the chitosan solution is to mix the crosslinking agent with chitosan during preparation of the solution. Another suitable crosslinking agent comprises a metal ion with more than two positive charges, such as $Ca^{2+}$, $Al^{3+}$, $Fe^{3+}$, $Ce^{3+}$, $Ce^{4+}$, $Ti^{4+}$, $Zr^{4+}$, and $Cr^{3+}$. Since the cations on chitosan possess antimicrobial properties, it is preferred herein to not use a crosslinking agent reacting to the cations, unless no alternative crosslinking agent is available.

In the embodiment herein where crosslinking agents are used, a suitable amount of crosslinking agent is from 0.001 to 30 weight percent based on the total dry weight of chitosan used to prepare the crosslinked-chitosan, more specifically from 0.02 to 20 weight percent, more specifically from 0.05 to 10 weight percent and most preferably from 0.1 to 5 weight percent.

Modified chitosans for use herein are any chitosan where the glucan chains carry pendant groups. Examples of such modified chitosans include carboxymethyl chitosan, methyl pyrrolidinone chitosan, glycol chitosan and the like. Methyl pyrrolidone chitosan is for instance described in U.S. Pat. No. 5,378,472, incorporated herein by reference. Water-soluble glycol chitosan and carboxymethyl chitosan are for instance described in WO87/07618, incorporated herein by reference Particularly suitable modified chitosans for use herein include water-soluble covalently bonded chitosan derivatives or tonically bonded chitosan derivatives obtained by contacting salt of chitosan with electrophilic organic reagents. Such water-soluble chitosan derivatives are described in EP-A737 692, which is herein incorporated by reference.

Suitable electrophilic organic reagents suitable for use for the preparation of chitosan derivatives contain from 2 to 18 carbon atoms or more per molecule and typically from 2 to 10 carbon atoms per molecule. In addition the electrophilic organic reagents contain groups, which are reactive, i.e. capable of forming a covalent bond with a nucleophile. Typical electrophilic organic reagents include, for example, ethylene oxide, propylene oxide, butylene oxide, glycidol, 3-chloro-1,2-propanediol, methyl chloride, ethyl chloride, isatoic anhydride, succinic anhydride, octenylsuccinic anhydride, acetic anhydride, gamma-butyrolactone, b-propiolactone, 1,3-propanesultone, acrylamide, glycidyltrimethyl ammonium chloride, glycidyldimethyl alkylammonium chloride such as lauryl, sodium chlorosulfonate, dimethyl sulfate, sodium chloroethanesulfonate, monochloroacetic acid, alkyl phenyl glycidyl ethers, glycidyl trimethoxysilanes, 1,2-epoxy dodecane. One preferred class of electrophilic organic reagent includes those electrophilic organic reagents, which contain an epoxide group, at least one acid group, preferably a diacid group and have from 3 to 18, preferably from 3 to 6 carbon atoms per molecule. Other preferred electrophilic organic reagents include cis-electrophilic organic reagents and trans-electrophilic organic reagent, with cis-electrophilic organic reagents being especially preferred. The electrophilic organic reagent may react with either the free amine or the underivatized hydroxyl groups of the chitosan. It is known that the amine functionality of the chitosan is generally regarded as a stronger nucleophilic site than the hydroxyl groups. Consequently weaker electrophiles will tend to react more readily with the amine groups than with the hydroxyl groups of the chitosan.

Preferably an effective amount of electrophilic organic reagent is substituted onto the chitosan to achieve the desired properties of the chitosan derivative, namely its water-soluble properties. Typically the chitosan derivatives suitable for use herein (modified chitosan) have a MS of from 0.03 to 10 moles of the electrophilic organic reagent per mole of glucosamine monomer unit. The term molar substitution (MS), means the moles of electrophilic organic reagent substituted on the chitosan per mole of glucosamine monomer unit.

In addition further modified chitosan can be prepared which contain other substituent groups, such as hydroxalkyl ether group (e.g., hydroxyethyl or hydroxypropyl ether groups), carboxyalkyl ether groups (e.g., carboxymethyl group), amide groups (e.g., succinyl groups), ester groups (e.g., acetate groups) or amino groups (e.g., 3-(trimethylammonium chloride)-2-hydroxylpropyl or 3-(dimethyloctadecylammonium chloride)-2-hydroxpropyl ether groups) in addition to the electrophilic organic reagent groups. These other substituent groups may be introduced prior to or subsequent to the reaction with the electrophilic organic reagent, or introduced simultaneously by reaction of the chitosan salt with the electrophilic organic reagent and the other derivatizing reagent.

Typically such covalently bonded chitosan derivative might be obtainable by a process which includes the step of (a) dispersing a salt of chitosan (e.g., any one of those described herein before) in an effective amount of an aqueous caustic medium to form a neutralized chitosan containing free amine groups, (b) introducing an electrophilic organic reagent in the slurry and (c) maintaining the slurry at a temperature and time effective to promote the substitution of the electrophilic organic reagent onto the chitosan to form a covalently bonded chitosan derivative and the dissolution of the covalently bonded chitosan into the aqueous medium. The chitosan derivatives can be prepared in either salt form, i.e., ionically bonded, or in the covalently bonded from. Processes for the preparation of such chitosan derivatives are described in depth in EP-A-737 692, incorporated herein by reference.

Suitable chitosans are commercially available from numerous vendors. Exemplary of a commercially available chitosan materials are those available from for example the Vanson Company. The preferred chitosan salt for use herein is chitosan pyrrolidone carboxylate (also called chitosonium pyrrolidone carboxylate), which has a degree of deacetylation of more than 85%, a water solubility of 1% (1 gram is soluble in 100 grams of distilled water at 25° C. and one atmosphere), a pH of 4.5, and a viscosity between 100–300 cps. Thus chitosonium pyrrolidone carboxylate is commercially available under the name Kytamer® PC from Amerchol Corporation.

Typically, the articles like disposable absorbent articles comprise chitosan material or a mixture thereof at a level of from 0.5 gm$^{-2}$ to 500 gm$^{-2}$, preferably from 1 to 200 gm$^{-2}$, more preferably from 3 gm$^{-2}$ to 100 gm$^{-2}$ and most preferably from 4 gm$^{-2}$ to 50 gm$^{-2}$ Anionic Absorbent Gelling Materials According to the present invention the articles comprise as an essential component an anionic absorbent gelling material (sometimes referred to as "super-sorber").

By anionic absorbent gelling materials it is meant herein absorbent gelling materials, which are predominantly negatively charged. These absorbent gelling materials can be any material having superabsorbent properties in which the functional groups are anionic, namely sulphonic groups, sulphate groups, phosphate groups or carboxyl groups. Preferably the functional groups are carboxyl groups. Particularly preferred anionic absorbent gelling materials for use herein are synthetic anionic absorbent gelling materials. Synthetic anionic absorbent gelling materials are preferred herein as they deliver higher odor and fluid absorption performance, this even under pressure, as compared to the absorption performance associated with natural anionic absorbent gelling materials like anionic polysaccharides when used in the same absorbent article.

Generally the functional groups are attached to a slightly cross-linked acrylic base polymer. For example the base polymer may be a polyacrylamide, polyvinyl alcohol, ethylene maleic anhydride copolymer, polyvinylether, polyvinyl sulphonic acid, polyacrylic acid, polyvinylpyrrolidone and polyvinylmorpholine. Copolymers of these monomers can also be used. Particular base polymers include cross-linked polyacrylates, hydrolyzed acrylonitrile grafted starch, starch polyacrylates and isobutylene maleic anhydride copolymers.

Such materials form hydrogels on contact with water (e.g., with urine, blood, and the like). One highly preferred type of hydrogel-forming, absorbent gelling material is based on polyacids, especially polyacrylic acid. Hydrogel-forming polymeric materials of this type are those, which, upon contact with fluids (i.e., liquids) such as water or body fluids, imbibe such fluids and thereby form hydrogels. These preferred absorbent gelling materials will generally comprise substantially water-insoluble, slightly cross-linked, partially neutralized, hydrogel-forming polymer materials prepared from polymerisable, unsaturated, acid-containing monomers. In such materials, the polymeric component formed from unsaturated, acid-containing monomers may comprise the entire gelling agent or may be grafted onto other types of polymer moieties such as starch or cellulose. Acrylic acid grafted starch materials are of this latter type. Thus, the preferred absorbent gelling materials include hydrolyzed acrylonitrile grafted starch, acrylic acid grafted starch, polyacrylates, maleic anhydride-based copolymers and combinations thereof. Especially preferred anionic absorbent gelling materials are the polyacrylates and acrylic acid grafted starch.

Whatever the nature of the polymer components of the preferred absorbent gelling materials, such materials will in general be slightly cross-linked. Crosslinking serves to render these preferred hydrogel-forming absorbent materials substantially water-insoluble, and cross-linking also in part determines the gel volume and extractable polymer characteristics of the hydrogels formed there from. Suitable cross-linking agents are well known in the art and include, for example, (1) compounds having at least two polymerisable double bonds; (2) compounds having at least one polymerisable double bond and at least one functional group reactive with the acid-containing monomer material; (3) compounds having at least two functional groups reactive with the acid-containing monomer materials; and (4) polyvalent metal compounds which can from ionic cross-linkages. Cross-linking agents of the foregoing types are described in greater detail in Masuda et al; U.S. Pat. No. 4,076,663; Issued Feb. 28, 1978. Preferred cross-linking agents are the di- or polyesters of unsaturated mono- or polycarboxylic acids with polyols, the bisacrylamides and the di-or triallyl amines. Especially preferred cross-linking agents are N,N'-methylenebisacrylamide, trimethylol propane triacrylate and triallyl amine. The cross-linking agent will generally comprise from about 0.001 mole percent to 5 mole percent of the preferred materials. More preferably, the cross-linking agent will comprise from about 0.01 mole percent to 3 mole percent of the gelling materials used herein.

The preferred absorbent gelling materials used herein are those which have a relatively high capacity for imbibing fluids encountered in the absorbent articles; this capacity can be quantified by referencing the "gel volume" of said absorbent gelling materials. Gel volume can be defined in terms of the amount of synthetic urine absorbed by any given absorbent gelling agent buffer and is specified as grams of synthetic urine per gram of gelling agent.

Gel volume in synthetic urine (see Brandt, et al, below) can be determined by forming a suspension of about 0.1–0.2 parts of dried absorbent gelling material to be tested with about 20 parts of synthetic urine. This suspension is maintained at ambient temperature under gentle stirring for about 1 hour so that swelling equilibrium is attained. The gel volume (grams of synthetic urine per gram of absorbent gelling material) is then calculated from the weight fraction of the gelling agent in the suspension and the ratio of the liquid volume excluded from the formed hydrogel to the total volume of the suspension. The preferred absorbent gelling materials useful in this invention will have a gel volume of from about 20 to 70 grams, more preferably from about 30 to 60 grams, of synthetic urine per gram of absorbent gelling material.

Another feature of the most highly preferred absorbent gelling materials relates to the level of extractable polymer material present in said materials. Extractable polymer levels can be determined by contacting a sample of preferred absorbent gelling material with a synthetic urine solution for the substantial period of time (e.g., at least 16 hours) which is needed to reach extraction equilibrium, by then filtering the formed hydrogel from the supernatant liquid, and finally by then determining the polymer content of the filtrate. The particular procedure used to determine extractable polymer content of the preferred absorbent gelling agent buffers herein is set forth in Brandt, Goldman and Inglin; U.S. Pat. No. 4,654,039; Issues Mar. 31, 1987, Reissue 32,649, The absorbent gelling materials which are especially useful in the absorbent articles herein are those which have an equilibrium extractable content in synthetic urine of no more than about 17%, preferably no more than about 10% by weight of the absorbent gelling material.

The preferred, slightly cross-linked, hydrogel-forming absorbent gelling materials will generally be employed in their partially neutralized form. For purposes described herein, such materials are considered partially neutralized when at least 25 mole percent of monomers used to form the polymer are acid group-containing monomers, which have been neutralized with a salt-forming cation. Suitable salt-forming cations include alkali metal, ammonium, substituted ammonium and amines. This percentage of the total monomers utilized, which are neutralized acid group-containing monomers, is referred to as the "degree of neutralization". Commercially available anionic absorbent gelling materials typically have a degree of neutralization somewhat from 25% to 90%. Highly preferred for use herein are anionic absorbent gelling materials having a degree of neutralization of 50% to 90% and most preferably from 60% to 85%.

The absorbent gelling materials herein before described are typically used in the form of discrete particles. Such absorbent gelling materials can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of absorbent gelling material particles may also be used.

The size of the absorbent gelling material particles may vary over a wide range. For reason of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Preferred for use herein are absorbent gelling material particles substantially all of which have a particle size of from about 30 microns to about 2 mm. "Particle Size" as used herein means the weighted average of the smallest dimension of the individual particles.

The amount of absorbent gelling material particles used in absorbent article will typically range from 0.5 $gm^{-2}$ to 500 $gm^{-2}$, preferably from 1 $gm^{-2}$ to 250 $gm^{-2}$, more preferably from 7 $gm^{-2}$ to 150$gm^{-2}$, and most preferably from 10 $gm^{-2}$ to 85 $gm^{-2}$.

The present invention is based on the finding that the addition of anionic absorbent gelling material on top of chitosan material, results in improved odor control performance over a wide range of malodorous components. Without to be bound by any theory this is mainly due to the ability of the anionic absorbent gelling material of enhancing the cationic properties of chitosan material as described herein before.

Advantageously combining of anionic absorbent gelling materials, namely synthetic anionic absorbent gelling materials as described herein (typically having a degree of neutralization of from 25% to 90%), together with chitosan material, also results in improved absorption capability not only towards water but also towards electrolytes-containing solutions. More particularly, in a preferred embodiment herein, wherein both the anionic absorbent gelling material and the chitosan material are present in salt form (have a high percentage of charged groups in their structures), said improved absorption capability is available immediately after exposure of the mixture of the two materials to electrolyte-containing solutions and last for a prolonged wearing time of the article by the user.

Whilst not wishing to be bound by any particular theory, it is believed that the combination of two materials results in improved absorbency due to the following facts:

Both chitosan materials and the anionic absorbent gelling materials are in salt form that is the form in which they act as fluid absorbent There is a reduction of salt poisoning effect thanks to the capacity of the cationic chitosan material to link anionic molecules in contact with bodily fluid (de-ionizing effect)

Furthermore the use of anionic absorbent gelling materials, namely synthetic anionic absorbent gelling materials as described herein (typically having a degree of neutralization of from 25% to 90%) on top of chitosan materials (preferably chitosan salts), in an absorbent article, exhibit high gel strength during fluid absorption. Indeed this combination results in improved absorption capacity under load conditions, in reduced rewetting and wetting through and hence improved comfort.

In a preferred embodiment according to the present invention chitosan material and the anionic absorbent gelling material are present in the absorbent article at a weight ratio of chitosan material to absorbent gelling material of from 10:1 to 1:10, preferably from 5:1 to 1:5, more preferably from 3:1 to 1:3 and most preferably from 2:1 to 1:2.

These ratios are preferred herein as it is within these ratio ranges that optimum performance is obtained for both odor control and fluid handling/absorption properties. Indeed operating outside this range in excess of anionic absorbent gelling material (i.e., ratio of more than 1:10 of chitosan material to anionic absorbent gelling material) is in favor of increased fluid absorption performance with reduced gel blocking effect but with more limited odor control performance. Indeed further increasing the presence of anionic absorbent gelling material will reduce the contact of the bodily fluid with the chitosan material, thus its odor control performance. On the other hand operating outside this range in excess of chitosan (i.e., ratio of more than 10:1 of chitosan material to anionic absorbent gelling material) is in favor of an increased odor control performance (as the contact of the microorganisms and nutriments thereof with chitosan materials is increased) but also increased gel-blocking effect. Indeed chitosan material have an extraordinarily high swellability, the swelling time being in the range of approximately 5 seconds, which results in formation of barrier layers, thereby preventing leakage through. However upon subsequent discharge of fluid these barriers resulting from the rapid swelling of chitosan material have the disadvantage that they may prevent the chitosan material particles not yet swollen from coming in touch with bodily fluid, these particles no longer functioning as swellable material or odor control material.

It is typically within the weight ratio ranges mentioned above that the anionic absorbent gelling agent will enhance the cationic properties of the chitosan material without hidden it from direct contact with bodily fluids, thereby resulting in optimum odor control and optimum fluid handling properties.

Optional Agents

The articles according to the present invention preferably further comprise on top of chitosan material and the absorbent gelling material, optional conventional agents or mixtures thereof.

For instance additional odor control agent or combinations thereof, known in the art for this purpose may be used herein. These agents can typically be classified according to the type of odor the agent is intended to combat. Odors may be chemically classified as being acidic, basic or neutral.

Alternatively, the odor control agents may be categorized with respect to the mechanism by which the malodor detection is reduced or prevented. For example, odor control agents which chemically react with malodorous compounds or with compounds which produce malodorous degradation products thereby generating compounds lacking odor or having an odor acceptable to consumers may also be utilized herein.

Suitable odor control agents for use herein typically include carbonates (e.g., sodium carbonate), bicarbonates (e.g., sodium bicarbonate), phosphates (e.g., sodium phosphate), sulphates (e.g., zinc and copper sulphates), carboxylic acids such as citric acid, lauric acid, boric acid, adipic acid and maleic acid, activated carbons, clays, zeolites, silicas, diatomaceous earth, and cyclodextrine. Such odor control agents and systems are disclosed in more details hereinafter and for example in EP-A-348 978, EP-A-510 619, WO 91/12029, WO 91/11977, WO 91/12030, WO 81/01643 and WO 96/06589.

Suitable odor control agents also include chelating agents and may be selected from amino carboxylates such as for example ethylenediamine-tetracetate, as described for example in U.S. Pat. No. 4,356,190, amino phosphonates such as ethylenediaminetetrakis (methylene-phosphonates), polyfunctional-substituted aromatic chelating agents as described in U.S. Pat. No. 3,812,044 and mixtures thereof. Without intending to be bound by theory it is believed that the benefit of these materials is in part due to their exceptional ability to remove iron, copper, calcium, magnesium and manganese ions present in the absorbed fluids and their degradation products by the formation of chelates.

Another suitable odor control agent for use herein is an acidic pH buffer system, such as citric acid and sodium bicarbonate, sodium phosphate and sorbic acid buffer systems. Such acidic pH buffer system will contribute to the benefits of the present invention by further enhancing and maintaining the cationic properties of the chitosan materials herein, even upon aging of the bodily fluid, i.e., upon prolonged wearing time of an article by the user.

Alternative odor control agents are ion exchange resins such as those described in U.S. Pat. No. 4,289,513 and U.S. Pat. No. 3,340,875.

Masking agents such as perfumes may also be used as odor control agents herein.

Typically, the articles like disposable absorbent articles may comprise the additional odor control agent or a mixture thereof at a level of from 0.5 $gm^{-2}$ to 600 $gm^{-2}$, preferably from 5 to 500 $gm^{-2}$, more preferably from 10 $gm^{-2}$ to 350 $gm^{-2}$ and most preferably from 20 $gm^{-2}$ to 200 $gm^{-2}$ The Absorbent Article Chitosan material and the anionic absorbent gelling material may be incorporated into the absorbent article by any of the methods disclosed in the art, for example layered on the core of the absorbent article or mixed within the fibers of the absorbent core.

Chitosan material and the anionic absorbent gelling material as described herein and optional additional odor control agent(s) are preferably incorporated between two layers of cellulose tissue. Optionally the system may be bonded between two cellulose tissue layers with, for example, a hot melt adhesive or any suitable bonding system, as described in WO 94/01069.

In one embodiment of the present invention chitosan, the anionic absorbent gelling material and optional additional odor control agent are incorporated in a layered structure in accordance with the disclosure of WO 94/01069 or Italian patent application number TO 93A 001028. TO 93A 001028 describes a layered structure substantially as described in WO 94/01069 with the exception that TO 93A 001028 comprises a much higher quantity of absorbent gelling material in the intermediate layer which is between the fibrous layers (120$gm^{-2}$) that would be incorporated in the present invention. The intermediate layer comprises in particular a polyethylene powder as thermoplastic material, which is mixed with the chitosan material and absorbent gelling material as described herein. The mixture is then heated such that the polyethylene melts and glues the laminate layers together. Adhesive lines are preferably also placed on the edges of the laminate to ensure that the edges of the laminate stick and any loose chitosan material and absorbent gelling material and optional additional odor control agent present do not fall out of the laminate.

Alternatively, the polyethylene powder may be replaced by a conventional glue for instance those commercially available from ATO Findley under the name H20-31® to glue the laminate layers and/or components together. Advantageously this method step allows to avoid the heating step necessary when using polyethylene powder.

The chitosan material and anionic absorbent gelling material may be distributed together or separately, homogeneously or non homogeneously, over the entire absorbent article or in at least one or several layers of the topsheet and/or backsheet or in at least one or several layers of the core or any mixture thereof. The chitosan material and absorbent gelling material may be distributed homogeneously or non homogeneously on the whole surface of the desired layer or layers, or on one or several area of the surface layer/layers to which it is positioned (e.g. central area and/or surrounding area like the edges of a layer of the absorbent article) or mixtures thereof.

In a preferred embodiment of the present invention optimum odor control and fluid handling performance are obtained when the chitosan material and absorbent gelling material are in close physical proximity within said absorbent article. Close physical proximity as used herein encompasses particulates, granulates, flakes, noodles and extrudates containing the chitosan material together with the absorbent gelling material. Close physical proximity also encompasses powder mixture of the two separate materials, wherein the two materials are individually in the form of particulates, granules, flakes and like, adjacent to one another (i.e., without being part of the same particulates, granules, flakes, noodles and the like). By 'close physical proximity' it is actually meant that the chitosan material and the absorbent gelling material are in direct contact with each other as opposed to being physically separated by for example a layer and thus being present in different layers and thus not in direct/intimate contact.

The chitosan material as described herein, the absorbent gelling material and optional odor control agent if present may be incorporated as a powder, a granulate, a particulate or can be sprayed in the form of for example a chitosan-containing solution within the absorbent article. When used in a granulate or particulate form the chitosan material as described herein and the absorbent gelling material as well as an optional odor control agent may be granulated separately and then mixed together or granulated together.

Figure 2:
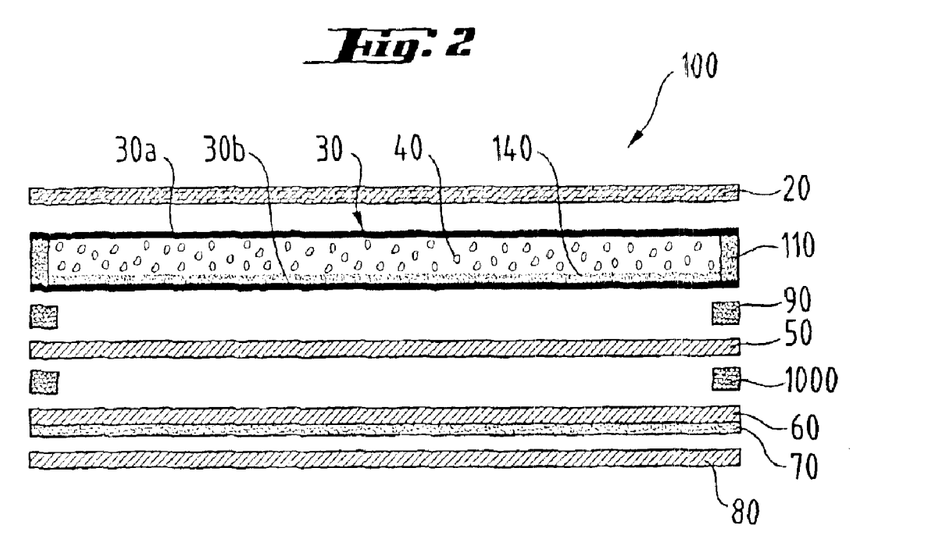
FIG. 2 shows a cross sectional view of a pantiliner having a topsheet, a backsheet and an absorbent core comprising a first and a second tissue layers, wherein the absorbent gelling material is distributed between the first and second tissue layers and wherein the chitosan material is applied onto the inner surface of the second tissue layer.

In one embodiment the absorbent gelling material is positioned such that at least a portion of the fluid discharge comes into contact with said absorbent gelling material before the chitosan material. In particular, the absorbent gelling material is located towards the topsheet whereas the chitosan material is located further away from the topsheet than the absorbent gelling material, e.g., towards the backsheet. Preferably the absorbent gelling material is located in the core and the chitosan material is located in the core but further away from the topsheet than the absorbent gelling material. For example when a laminate of two fibrous layers is used as the absorbent core, chitosan material is typically located (for example sprayed) on the fibrous layer directed towards the backsheet (both sides of the layer are suitable although the inner side is preferred to ensure close physical proximity of the chitosan material to the absorbent gelling material present between the two fibrous layers) and the absorbent gelling material is located between the two layers of the laminate (i.e., the one directed to the topsheet and the one directed to the backsheet). This execution is illustrated in FIG. 2. Also chitosan material particles and the absorbent gelling material particles might be incorporated in reverse gradient concentration through the thickness of the absorbent core. This can be achieved by disposing chitosan material particles so as to form a gradient concentration through the thickness of the absorbent core, a so called Z-directional gradient, wherein the concentration of the chitosan materials increases from the surface of the absorbent core facing the topsheet to the surface of the absorbent core and by disposing the gelling absorbent material particles so as to form a gradient concentration through the thickness of the absorbent core, wherein the concentration of the absorbent gelling materials decreases from the surface of the absorbent core facing the topsheet to the surface of the absorbent core facing the backsheet. Such executions are particularly beneficial for optimum odor control and optimum fluid handling, i.e., optimum absorption and retention without any leakage through or rewetting occurrence. The chitosan material due to its gelifying properties forms a so-called impermeable layer towards the backsheet thereby preventing any leakage through.

Suitable disposable absorbent articles according to the present invention include those described as follows:

Absorbent Core

According to the present invention, the absorbent can include the following components: (a) an optional primary fluid distribution layer preferably together with a secondary optional fluid distribution layer; (b) a fluid storage layer; (c) an optional fibrous ("dusting") layer underlying the storage layer; and (d) other optional components. According to the present invention the absorbent may have any thickness depending on the end use envisioned.

a Primary/Secondary Fluid Distribution Layer

One optional component of the absorbent according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilized. The fluid distribution layers can be comprised of any material typical for such distribution layers. In particular fibrous layers maintain the capillaries between fibers even when wet are useful as distribution layers.

b Fluid Storage Layer

Positioned in fluid communication with, and typically underlying the primary or secondary distribution layers, is a fluid storage layer. The fluid storage layer typically comprises the chitosan material and/or any usual absorbent gelling material. It preferably comprises such materials in combination with suitable carriers.

Suitable carriers include materials, which are conventionally utilized in absorbent structures such as natural, modified or synthetic fibers, particularly modified or non-modified cellulose fibers, in the form of fluff and/or tissues. Most preferred are tissue or tissue laminates in the context of sanitary napkins and panty liners.

An embodiment of the absorbent structure made according to the present invention may comprise multiple layers comprises a double layer tissue laminate typically formed by folding the tissue onto itself. These layers can be joined to each other for example by adhesive or by mechanical interlocking or by hydrogen bridge bands. Chitosan materials and/or absorbent gelling materials and/or other optional materials can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the chitosan materials and/or absorbent gelling materials are dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing chitosan materials and/or absorbent gelling materials partially or fully.

c Optional Fibrous ("Dusting") Layer

An optional component for inclusion in the absorbent core according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the Absorbent Structure

The absorbent core according to the present invention can include other optional components normally present in absorbent webs. For example, a reinforcing scrim can be positioned within the respective layers, or between the respective layers, of the absorbent core. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

The Topsheet

According to the present invention the absorbent article comprises as an essential component a topsheet. The topsheet may comprise a single layer or a multiplicity of layers. In a preferred embodiment the topsheet comprises a first layer, which provides the user-facing surface of the topsheet and a second layer (also called secondary topsheet) between the first layer and the absorbent structure/core.

The topsheet as a whole and hence each layer individually needs to be compliant, soft feeling, and non-irritating to the wearer's skin. It also can have elastic characteristics allowing it to be stretched in one or two directions. According to the present invention the topsheet may be formed from any of the materials available for this purpose and known in the art, such as woven and non-woven fabrics and films. In a preferred embodiment of the present invention at least one of the layers, preferably the upper layer, of the topsheet comprises a hydrophobic, liquid permeable apertured polymeric film. Preferably, the upper layer is provided by a film material having apertures, which are provided to facilitate liquid transport from the wearer-facing surface towards the absorbent structure. Such apertured polymeric topsheet further participates to the odor control benefit. If present the lower layer preferably comprises a non-woven layer, an apertured formed film or an air laid tissue.

The Backsheet

The backsheet primarily prevents the extrudes absorbed and contained in the absorbent structure from wetting articles that contact the absorbent product such as underpants, pants, pajamas and undergarments. The backsheet is preferably impervious to liquids (e.g. menses and/or urine) and is preferably manufactured from a thin plastic film, although other flexible liquid impervious materials can also be used. As used herein, the term "flexible" refers to materials that are compliant and will readily conform to the general shape and contours of the human body. The backsheet also can have elastic characteristics allowing it to stretch in one or two directions. In a preferred embodiment the backsheet comprises a first layer, which provides the garment-facing surface of the backsheet and a second layer (also called secondary backsheet) between the first layer and the absorbent structure/core.

The backsheet typically extends across the whole of the absorbent structure and can extend into and form part of or all of the preferred side flaps, side wrapping elements or wings.

The backsheet can comprise a woven or nonwoven material, polymeric films such as thermoplastic films of polyethylene or polypropylene, or composite materials such as a film-coated nonwoven material. Preferably, the backsheet is a polyethylene film typically having a thickness of from about 0.012 mm (0.5 mil) to about 0.051 mm (2.0 mil).

Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matt finished to provide a more cloth like appearance. Further, the backsheet can permit vapors to escape from the absorbent structure, i.e. be breathable, while still preventing extrudates from passing through the backsheet. Also breathable backsheets comprising several layers, e.g. film plus non-woven structures, can be used. Breathable may be preferred herein as they contribute to further improve the odor control benefit associated with the present invention. Even more preferred herein the disposable absorbent articles have both a breathable backsheet and an apertured polymeric film topsheet for further increasing the odor control performance of the articles.

Odor Control Test

The odor reduction is measured by for example an in vitro sniff test. In vitro sniff test consists in analyzing by expert graders the odor associated with articles comprising the ingredients to be tested (including references articles) when contacted with an odorous components-containing solution.

The expert graders express their judgment about (un) pleasantness of the odor using a (un)pleasantness scale, typically from −10 (highest level of unpleasantness) to 5 (most pleasant). With this procedure, each grader compares MU (Unpleasantness) in the test session. The relative MU odor values from different products are assigned numbers. For example, in a test session, a sample that is perceived to be twice as strong as another is assigned twice as large a number. One that is perceived to be one-tenth as strong as another is assigned a number one-tenth as large, etc. In each test session, zero is used to designate neutral hedonicity, and + and − numbers are assigned in ratio proportion to the relative pleasantness and unpleasantness of the odor.

Surprisingly in vitro in-house sniff tests conducted by using an in-house odorous components-containing solution reproducing the essential malodorous characteristics of menses showed synergistic odor reduction when comparing chitosan (e.g. chitosonium pyrrolidone carboxylate (Kytamer®) together with an absorbent gelling material (e.g., cross-linked sodium polyacrylate XZ 9589001 available from Dow Chemicals) to each of these ingredients taken alone at the same total level of active. Indeed the % of unpleasantness reduction obtained for this mixture was higher than the % of unpleasantness reduction obtained for each of the two ingredients used alone at the same total level of active in same articles. The Unpleasantness values, for each sample, were obtained as a mean of at least 15 observations (3 products, 5 graders). These results were statistically significant.

Alternatively the odor reduction can also be measured with in vivo sniff tests as described in patent applications, EP-A-811387 or WO97/46191, herein incorporated by reference.

The present invention is further illustrated by the following example.

EXAMPLES

Example A

The feminine pads used in the following examples were Always (Always is a registered Trade Mark) as sold by the Procter & Gamble Company.

Each feminine pad was opened by cutting the wrap around the perforated coverstock at its bottom face approximately along a longitudinal edge of the release paper, which covers the external adhesive layer. The side of the absorbent fibrous core was then exposed by slightly shifting the water impermeable plastic bottom layer and subsequently, the fibrous core was split into two halves, each having approximately the same thickness, along a plane, which is parallel to the plane of the napkin itself. The chitosan material and anionic absorbent gelling material (AGM) were homogeneously distributed between these tow fibrous layers, which were then joined together to reconstitute the absorbent core.

The water impermeable inner backsheet was then put back into its original position and the wrap around perforated coverstock was sealed along the cut by means of e.g. a double-sided adhesive tape.

Samples were produced using the method above, wherein the AGM (0.5 g) used was crosslinked sodium polyacrylate XZ 9589001 available from Dow Chemicals and chitosan material (0.5 g) used was chitosonium pyrrolidone carboxylate commercially available from Amerchol Corporation under the name Kytamer® PC.

Example B

Other pads were prepared by following the method in Example A except that instead of distributing homogeneously the two powders, chitosan material and AGM, a chitosan solution was prepared and sprayed on the lower halve fibrous layer (i.e., the one intended to be closer to the backsheet of the pad once reconstituted) and that AGM was distributed between the two air laid layers as described in example A.

The water impermeable inner backsheet was then put back into its original position and the wrap around perforated coverstock was sealed along the cut by means of e.g. a double-sided adhesive tape.

The AGM (0.5 g) used was cross-linked sodium polyacrylate XZ 9589001 available from Dow Chemicals.

The chitosan solution was prepared by solubilizing 1 g of chitosonium pyrrolidone carboxylate commercially available from Amerchol Corporation under the name Kytamer® PC in 100 g of distilled water and stirring at 40° C. over 1 night. 10 g of the prepared solution was sprayed onto the lower halve of the fibrous layer (i.e., 0.1 g of chitosan per pad)

Example C

Other pads were prepared by following the method in Example A except that silicate (odor control agent) was added on top of absorbent gelling material (AGM) and chitosan material in Example A. Accordingly the three ingredients were homogeneously distributed between these two fibrous layers which were then joined together to reconstitute the absorbent core.

The chitosan material (0.4 g) used was chitosonium pyrrolidone carboxylate commercially available from Amerchol Corporation under the name Kytamere® PC. AGM (0.4 g) used was cross-linked sodium polyacrylate XZ 9589001 available from Dow Chemicals. Silicate used (0.7 g) was Silica gel 123 available from Grace

Example D

The feminine pantiliner used in the following examples is a modified panty liner based on Always "Alldays Duo Active" manufactured by Procter & Gamble, Germany. The topsheet is a film/non woven composite {film supplier code BPC 5105 CPM BP Chemical Germany, non-woven supplier code ARBO TB/BI Mequinenza Spain}. The core material is a tissue laminate (13.2 cm×4.0 cm) composed of a 2 layers of air laid tissue of 55 g/m² basis weight {available from Unikay Italy under the supplier code Unikay 303 LF}. Between the two tissue layers the laminate contains chitosan material together with anionic absorbent gelling material.

The backsheet comprises two layers a first layer and a second layer. The first layer is in contact with the absorbent tissue and the second layer. The second layer is in contact with the first layer and the undergarment of the wearer. The first layer is a formed apertured film (CPT) made of Low Density PE {supplied by Tredegar Film Products B.V. Holland under the manufacturing code X-1522}. The second layer is composed of a nonwoven laminate {13 MB/16 SB manufactured by Corovin GmbH in Germany under the trade name MD 2005}. The nonwoven laminate is composed of 16 g/m² spun bond and 13 g/m² meltblown. Each backsheet layer is joined over the full surface by an extensively overlapped spiral glue application at a basis weight of approximately 8 g/m². The glue utilized for attachment of both backsheet layers was supplied by SAVARE' SpA. Italy (under the material code PM17).

The AGM (0.5 g) used was cross-linked sodium polyacrylate XZ 9589001 available from Dow Chemicals and chitosan material (0.5 g) used was chitosonium pyrrolidone carboxylate commercially available from Amerchol under the name Kytamer® PC.

Figure 1:
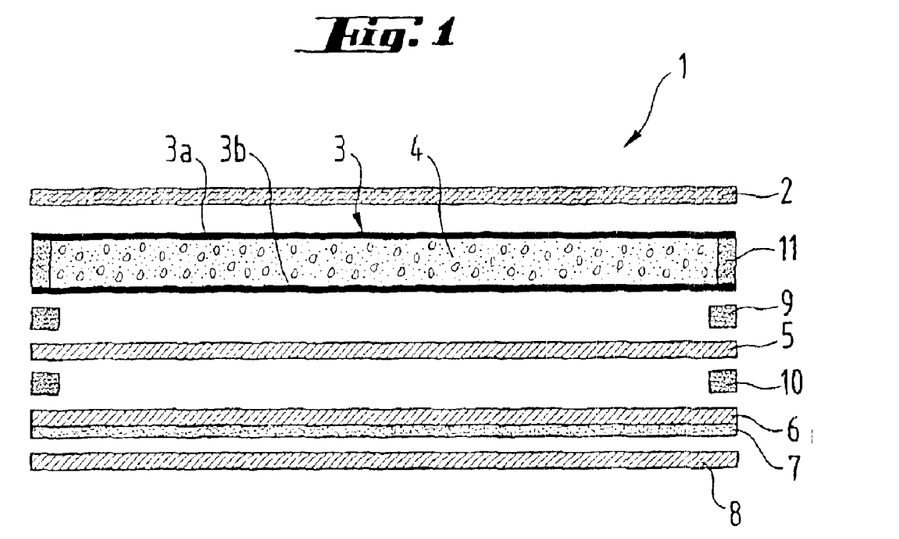
FIG. 1 shows a cross sectional view of a pantiliner having a topsheet, a backsheet and an absorbent core comprising a first and a second tissue layers, the chitosan material and anionic absorbent gelling material are incorporated between said first and second tissue layers.

FIG. 1 represents a sectional view of a pantiliner structure 1 of Example D which comprises a topsheet 2, air laid tissue layers 3 comprising a first 3a and second 3b tissue layers joined at their longitudinal edges with adhesive area 11, a mixture 4 of chitosonium pyrrolidone carboxylate powder and absorbent gelling material is present between the first and second air laid tissue layers 3a and 3b, a backsheet comprising a first layer 5 and a second layer 6, adhesive area 9 and 10, an adhesive layer 7 and a removable release liner 8.

Other panty liners can be made starting from Example D above with similar modifications regarding the incorporation of the chitosan material and absorbent gelling material as described in Examples B to C.

For example FIG. 2 represents a sectional view of a pantiliner structure 100 which comprises a topsheet 20, air laid tissue layers 30 comprising a first and a second tissue layers 30a and 30b joined at their longitudinal edges with adhesive area 110, absorbent gelling material particles 40 located between the first and second air laid tissue layers 30a and 30b, chitosonium pyrrolidone carboxylate 140 located on the inner surface of the second air laid tissue 30b, a backsheet comprising a first layer 50 and a second layer 60, adhesive area 90 and 1000, an adhesive layer 70 and a removable release liner 80.

All the above-exemplified absorbent articles delivered outstanding odor control benefits and fluid handling benefits when coming into contact with bodily fluids like menses.

What is claimed is:

1. An article comprising chitosan material and an anionic absorbent gelling material.

2. An article according to claim 1 wherein said article is a disposable absorbent article, selected from the group consisting of a sanitary napkin, pantiliner, tampon, diaper, incontinent pad, breast pad, perspiration pad or interlabial pad or a body cleaning article.

3. An article according to claim 2 wherein said article is a disposable absorbent article comprising a liquid pervious topsheet, a backsheet and an absorbent core intermediate said backsheet and said topsheet.

4. An article according to claim 1 wherein the chitosan material has a degree of deacetylation of more than 75%.

5. An article according to claim 4 wherein the chitosan material has a degree of deacetylation from about 80% to about 100%.

6. An article according to claim 1 wherein the chitosan material is water-soluble.

7. An article according to claim 1 wherein the chitosan material has an acidic pH typically within the range of about 3 to about 6.

8. An article according to claim 1 wherein the chitosan material is a chitosan salt, a chitosan salt of citric acid, formic acid, acetic acid, N-acetylglycine, acetylsalicylic acid, fumaric acid, glycolic acid, iminodiacetic acid, itaconic acid, lactic acid, maleic acid, malic acid, nicotinic acid, salicylic acid, succinamic acid, succinic acid, ascorbic acid, aspartic acid, glutamic acid, glutaric acid, malonic acid, pyruvic acid, sulfonyldiacetic acid, benzoic acid, epoxysuccinic acid, adipic acid, thiodiacetic acid, thioglycolic acid, alanine, valine, leucine, isoleucine, prolinephenylalanine, triptofane, metionine, glycine, serine, cysteine, tyrosine, asparagine, glutamine, lysine, arginine, istydine, hydroxyproline, pyrrolidone carboxylic acid, chitosonium pyrrolidone carboxylate and mixtures thereof.

9. An article according to claim 1 which comprises from about 0.5 $gm^{-2}$ to about 500 $gm^{-2}$ of the chitosan material or a mixture thereof.

10. An article according to claim 9 which comprises from about 1 to about 200 $gm^{-2}$ of the chitosan material or a mixture thereof.

11. An article according to claim 1 wherein the absorbent gelling material is a synthetic anionic absorbent gelling material having a degree of neutralization of from about 25% to about 90%.

12. An article according to claim 11 wherein the absorbent gelling material is hydrolyzed acrylonitrile grafted starch, acrylic acid grafted starch, polyacrylate, maleic anhydride-based copolymer, a polyacrylate and/or acrylic acid grafted starch and combinations thereof.

13. An article according to claim 1 wherein the chitosan material and the anionic absorbent gelling material are present in the article at a weight ratio of chitosan material to the absorbent gelling material of about 10:1 to about 1:10.

14. An article according to claim 11 wherein the chitosan material and the anionic absorbent gelling material are present in the article at a weight ratio of chitosan material to the absorbent gelling material of about 10:1 to about 1:10.

15. An article according to claim 1 further comprising an additional odor control agent, typically silicates, zeolites, diatomaceous earth, cyclodextrine, acidic pH buffer system, chelating agents, ion exchange resins, perfumes, activated carbons, clay or a mixture thereof.

16. An article according to claim 11 further comprising an additional odour control agent, typically silicates, zeolites, diatomaceous earth, cyclodextrine, acidic pH buffer system, chelating agents, ion exchange resins, perfumes, activated carbons, clay or a mixture thereof.

17. An article according to claim 13 further comprising an additional odor control agent, typically silicates, zeolites, diatomaceous earth, cyclodextrine, acidic pH buffer system, chelating agents, ion exchange resins, perfumes, activated carbons, clay or a mixture thereof.

18. An article according to claim 15, wherein the level of the additional odor control agent or a mixture thereof is from about 0.5 $gm^{-2}$ to about 600 $gm^{-2}$.

19. An article according to claim 16, wherein the level of the additional odor control agent or a mixture thereof is from about 0.5 $gm^{-2}$ to about 600 $gm^{-2}$.

20. An article according to claim 17, wherein the level of the additional odor control agent or a mixture thereof is from about 0.5 $gm^{-2}$ to about 600 $gm^{-2}$.

21. A method of controlling odour associated with bodily exudates and/or bodily fluids, wherein said bodily exudates and/or fluids are contacted with an odour control system comprising chitosan material together with an anionic absorbent gelling material.

* * * * *